US011826124B2

(12) United States Patent
Fei

(10) Patent No.: US 11,826,124 B2
(45) Date of Patent: Nov. 28, 2023

(54) APPARATUS AND METHOD FOR IMAGE-GUIDED INTERVENTIONS WITH HYPERSPECTRAL IMAGING

(71) Applicant: Board of Regents, The University of Texas System, Austin, TX (US)

(72) Inventor: Baowei Fei, Richardson, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 861 days.

(21) Appl. No.: 16/774,478

(22) Filed: Jan. 28, 2020

(65) Prior Publication Data
US 2020/0237229 A1 Jul. 30, 2020

Related U.S. Application Data

(60) Provisional application No. 62/798,299, filed on Jan. 29, 2019.

(51) Int. Cl.
*G06T 7/12* (2017.01)
*A61B 5/00* (2006.01)
(Continued)

(52) U.S. Cl.
CPC .......... *A61B 5/0075* (2013.01); *A61B 5/0077* (2013.01); *A61B 5/7445* (2013.01);
(Continued)

(58) Field of Classification Search
CPC ......... A61B 5/0077; A61B 3/12; A61B 3/113; A61B 3/1216; A61B 5/14532;
(Continued)

(56) References Cited

U.S. PATENT DOCUMENTS

2016/0007858 A1* 1/2016 Hendriks ............. A61B 5/0059
600/407
2017/0085855 A1* 3/2017 Roberts ................. A61B 5/377
2020/0260066 A1* 8/2020 Liu ....................... H04N 13/296

FOREIGN PATENT DOCUMENTS

WO WO 2018-075679 A1 4/2018

OTHER PUBLICATIONS

M. Halicek et al., "Deep convolutional neural networks for classifying head and neck cancer using hyperspectral imaging," J. Biomed. Opt. 22(6), pp. 060503-1 through 060503-4 (2017).
(Continued)

*Primary Examiner* — Masum Billah
(74) *Attorney, Agent, or Firm* — Stanek Lemon Crouse & Meeks, P.A.

(57) ABSTRACT

A hyperspectral imaging system can include a first hyperspectral imaging camera that is configured to provide first hyperspectral image data of an object in a first field of view. A second hyperspectral imaging camera can be separated from the first hyperspectral imaging camera, where the second hyperspectral imaging camera is configured to provide second hyperspectral image data of the object in a second field of view. A processor circuit can be operatively coupled to the first and second hyperspectral imaging cameras, where the processor circuit configured to combine the first and second hyperspectral image data to generate a hypercube of data for the object comprising spectral data included in the first and second hyperspectral image data.

17 Claims, 14 Drawing Sheets

(51) Int. Cl.
  *G06T 7/00* (2017.01)
  *G01N 21/25* (2006.01)
  *H04N 23/90* (2023.01)
  *H04N 23/695* (2023.01)

(52) U.S. Cl.
  CPC ........ *G01N 21/255* (2013.01); *G06T 7/0012* (2013.01); *H04N 23/695* (2023.01); *H04N 23/90* (2023.01); *G06T 2207/10036* (2013.01); *G06T 2207/20084* (2013.01); *G06T 2207/20212* (2013.01)

(58) Field of Classification Search
  CPC ....... A61B 5/6803; A61B 8/10; A61B 3/0008; A61B 2562/0204; A61B 2562/0219; A61B 2562/0247; A61B 3/0025; A61B 3/005; A61B 3/022; A61B 3/024; A61B 3/028; A61B 3/063; A61B 3/066; G06F 2111/06; G06F 2111/10; G06F 2113/08; G06F 2119/14; G06F 30/17

USPC ........................................................ 600/476
See application file for complete search history.

(56) References Cited

OTHER PUBLICATIONS

G. Lu et al., "Detection of Head and Neck Cancer in Surgical Specimens Using Quantitative Hyperspectral Imaging," Clin. Cancer Res., 23(18), Sep. 15, 2017, pp. 5426-5436.

G. Lu et al., "Medical hyperspectral imaging: a review," J. Biomed. Opt., 19(1), pp. 010901-1 through 010901-23 (2014).

B. Fei et al., "Label-free reflectance hyperspectral imaging for tumor margin assessment: a pilot study on surgical specimens of cancer patients," J. Biomed. Opt. 22(8), pp. 086009-1 through 086009-7 (2017).

* cited by examiner

APPARATUS AND METHOD FOR IMAGE-GUIDED INTERVENTIONS WITH HYPERSPECTRAL IMAGING

CROSS-REFERENCE TO RELATED APPLICATIONS AND CLAIM FOR PRIORITY

The present application claims priority to U.S. Provisional Patent Application Ser. No. 62/798,299 entitled "Apparatus and Method for Image-Guided Interventions with Hyperspectral Imaging Incorporating Cancer Detection," filed in the USPTO on Jan. 29, 2019, the entire disclosure of which is incorporated herein by reference.

FIELD OF THE INVENTION

This invention relates to ex vivo and in vivo hyperspectral imaging of tissue and the detection of cancerous tissue in near real-time or real-time.

BACKGROUND

Hyperspectral imaging (HSI) offers great potential for non-invasive disease diagnosis and surgical guidance. Light delivered to the biological tissue undergoes multiple scattering from inhomogeneity of biological structures and absorption primarily in hemoglobin, melanin and water as it propagates through tissue. It is assumed that the absorption, fluorescence and scattering characteristics of tissue change during the progression of disease, therefore the reflected, fluorescent and transmitted light from tissue captured by HSI carries quantitative diagnostic information about tissue pathology.

Biological tissues are heterogeneous in composition with spatial variations in optical properties. Light entering biological tissue can undergo multiple scattering and absorption events as it propagates across the tissue. Scattering occurs where there is a spatial variation in the refractive index. In cellular media, the light scatters include the subcellular organelles, with their size running from <100 nm to 6 µm. For example, mitochondria are light scatterers among the organelles. The structure of a lipid membrane and lipid folds running inside gives mitochondria a high optical contrast to the surrounding cytoplasm and produces the observed strong scattering effects. The shape and size of the cells vary among different tissue types with dimensions of a few microns and larger. Although an isolated cell can be a strong scatterer, within a tissue the scattering can be largely subcellular in origin. The scattering properties of support tissues composed of cells and extracellular proteins (elastin and collagen, etc.) are caused by the small-scale inhomogeneities and the large-scale variations in structures they form.

The penetration ability of light into biological tissues depends on how strongly the tissue absorbs light. Most tissue are sufficiently weak absorbers to permit significant light penetration within the therapeutic window, ranging from 600 to 1300 nm. Within the therapeutic window, scattering is over absorption, so the propagating light becomes diffuse. Tissue absorption is a function of molecular composition. Molecules absorb photons when the photon's energy matches an interval between internal energy states, and the transition between quantum states obeys the selection rules for the species. During absorption processing, transitions between two energy levels of a molecule that are well defined at specific wavelengths could serve as a spectral fingerprint of the molecule for diagnostic purposes. For example, absorption spectra can characterize the concentration and oxygen saturation of hemoglobin, which can signal two indicators of cancer: angiogenesis and hypermetabolism. Tissue components absorbing light are called chromophores. Some of the most important chromophores for visible wavelengths are blood and melanin, of which the absorption coefficient decreases monotonically with increasing wavelength. The primary absorber for UV wavelengths are protein and amino acids, while the important absorbing chromophore for IR wavelengths is water.

The light absorbed by tissue constituents (reduced nicotinamide adenine dinucleotide (NADH), hemoglobin, melanin, water, etc.) is either converted to heat or radiated in the form of luminescence including fluorescence and phosphorescence. Fluorescence that originates from endogenous fluorescent chromophores is also called autofluorescence. Incident light typically in the ultraviolet or visible region excites the tissue molecules and induces fluorescence emission. The majority of the endogenous fluorophores are associated with the structural matrix of tissue or with various cellular metabolic pathways. The most common fluorephores in the structural matrix are collagen and elastin, while the predominant fluorephores involved in cellular metabolism are the NADH, flavin adenine dinucleotide (FAD), and lipopigments. These intrinsic fluorophores exhibit different strengths and cover various spectral ranges in the ultraviolet and visible regions. For example, fluorescence from collagen or elastin using excitation between 300 and 400 nm shows broad emission bands between 400 and 600 nm, which can be used to distinguish various types of tissues, e.g., epithelial and connective tissue. Cells in different disease states often have different structures, or undergo different rate of metabolism, which result in different fluorescence emission spectra. Therefore, fluorescence imaging makes it possible to investigate tissues for diagnosis of diseases in real time without administrating exogenous fluorescent agents. Various exogenous fluorophores has also been created and studied for biological diagnostics using HSI.

Incident light can be directly reflected on the surface of the tissue, or be scattered due to random spatial variations in tissue density (membranes, nuclei, etc.) and then be remitted to the tissue surface. Light can become randomized in direction due to multiple scattering, known as diffuse reflectance, which provides information about scattering and absorbing components deep within the tissue. The measured reflectance signal represents light that has sampled a variety of sampling depths within the tissue, and may therefore be an average measure of the properties over a certain volume of tissue. Significant scatterers present in tissue include collagen, keratin, nuclei, and mitochondria; however, other smaller subcellular components (e.g., lysosomes, membranes) also scatter light. The reflectance signal measured from epithelial tissue is determined by the structural and biochemical properties of the tissue; therefore, analyzing changes in optical properties can be used to noninvasively probe the tissue microenvironment. Alterations in tissue morphology which are associated with disease progression can affect the scattering signal include hyperplasia, nuclear crowding, degradation of collagen in the extracellular matrix by matrix metalloproteinases (MMPs), and increased nuclear/cytoplasmic ratio. As a disease progress, hemoglobin absorption may be affected by angiogenesis and tissue hypoxia, etc.

Reflectance imaging can detect local changes in scattering and absorption of tissue, and fluorescence imaging can probe changes in the biochemical composition of tissue by revealing levels of endogenous fluorophores. Multimodal HSI combining reflectance and fluorescence has been investigated for cancer diagnosis. Furthermore, HSI system can be adapted to other existing techniques, such as microscope, and colposcope, to provide complementary information in a more accurate and reliable manner. Transmission HSI microscope is one example of these combinatory technologies and has been used in tissue pathology.

An HSI system can include a light source, wavelength dispersion devices and an area detector. The tissue sample illuminated by the light source is projected through a front lens into entrance slit which only passes light from a narrow line. After collimation, a dispersive device (such as prism, grating, etc.) splits the light into a series of narrow spectral bands that are then focused onto a detector array. Slit width controls the amount of light entering the spectrograph. In this way, for each pixel interval along the line defined by the slit, a corresponding spectrum is projected on a column of the detector array. Thus, each line of the targeted area on tissue sample is projected as a 2D image onto the detector, with one spatial dimension and one spectral dimension. By scanning over the tissue specimen or moving the camera across the tissue sample in a pushbroom or line-scanning fashion, HSI camera collects 2D images for adjacent lines, creating a hypercube with two spatial dimensions and one spectral dimension.

Current hyperspectral imaging for cancer detection uses a single camera with a few spectral bands. Furthermore, the current hyperspectral imaging system for cancer detection has a relatively low spectral resolution. Even with these limitations, HSI produces extremely large data sets. Furthermore, processing methodology for these large HSI data sets have not yet progressed to approach real-time video-like feedback of information to the operator, for example, a surgeon performing surgical resection of cancerous tissue.

BRIEF DESCRIPTION OF DRAWINGS

The illustrative embodiments, further objectives and features thereof, will best be understood by reference to the following detailed description of illustrative embodiments of the present disclosure when read in conjunction with the accompanying drawings, wherein.

DESCRIPTION OF THE EMBODIMENTS ACCORDING TO THE INVENTION

Figure 1A:
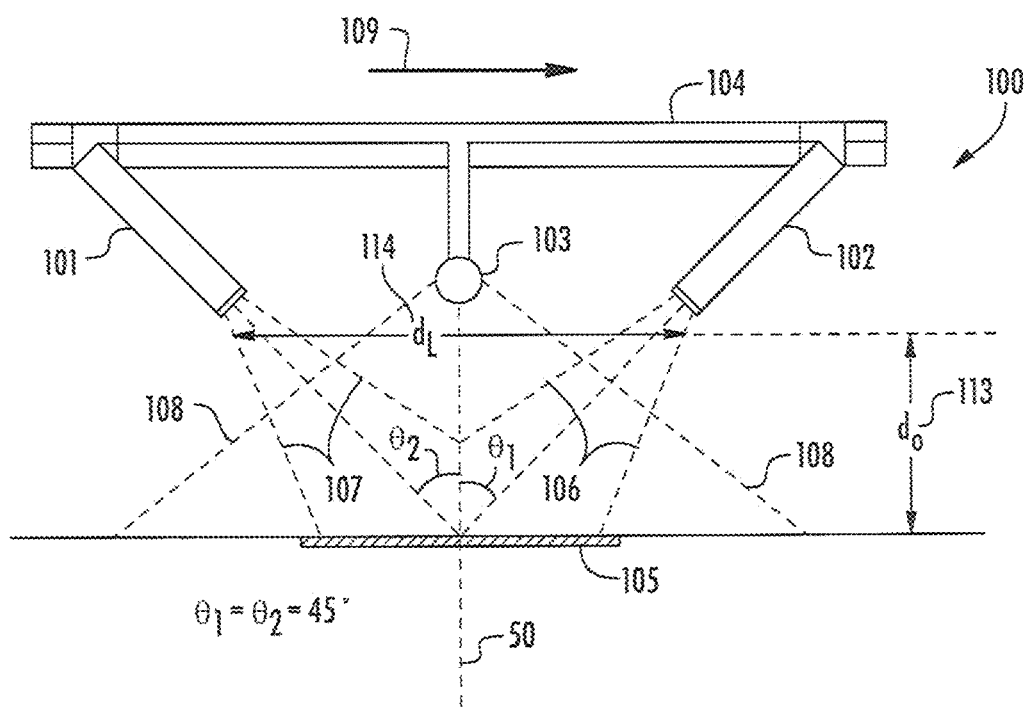
FIG. 1A is a schematic drawing of a hyperspectral imaging system in some embodiments according to the invention as viewed from one side. The system can include two hyperspectral imaging cameras, one for the visible and near infrared camera and the other one for the short-wave infrared camera. The two hyperspectral imaging cameras can be mounted on the frame and are controlled by a processor circuit system for image scanning. The two hyperspectral imaging cameras are placed at different angles (e.g., 45 degrees as shown in the graph) so that the field of views of the two hyperspectral imaging cameras are overlapped at the region of interest that can be tissue samples or objects. The light illumination may be located at the center for illuminating the samples or objects.

Exemplary embodiments of the present disclosure are described in detail with reference to the accompanying drawings. The disclosure may, however, be exemplified in many different forms and should not be construed as being limited to the specific exemplary embodiments set forth herein. Rather, these exemplary embodiments are provided so that this disclosure will be thorough and complete, and will fully convey the scope of the disclosure to those skilled in the art.

Hyperspectral imaging (HSI) is a hybrid modality that can combine imaging and spectroscopy. By collecting spectral information from two HSI cameras, each pixel of a two dimensional (2D) detector array (i.e., an HSI camera), HSI can provide a three dimensional (3D) dataset of spatial (2D) and spectral (1D) information, which can be referred to herein as a hypercube of data. With spatial information, the source of each spectrum on samples can be located, which makes it possible to probe more completely the light interactions with pathology. The spectral signature of each pixel in the images enables HSI to identify various pathological conditions. HSI generally covers a contiguous portion of the light spectrum with more spectral bands (up to a few hundreds) and higher spectral resolution than multispectral imaging (such as RGB color cameras), therefore, HSI is able to capture the subtle spectral differences under different pathological conditions while multispectral imaging may miss significant spectral information for diagnostics.

A two camera HSI system is disclosed which covers the visible light region and the short wave infrared region and uses hundreds of spectral bands in some embodiments according to the invention. The two camera HSI system also has a high spectral resolution (e.g., 2 nm). These features can improve the sensitivity for cancer detection as compared to the existing HSI systems. The configuration of the two camera system enables acquisition of a very large amount of optical spectral data over a broad spectral range. As the data size increases, the information and complexity may also increase and the need for novel and more efficient data processing methodologies arise.

The disclosed HSI systems can integrate multiple micro-hyperspectral cameras that cover visible and near-infrared (VNIR, e.g., 400 nm-1000 nm), extended VNIR (e.g., 600 nm-1700 nm) and shortwave infrared (SWIR, e.g., 900 nm-2500 nm) regions in some embodiments according to the invention. The InGaAs SWIR micro-camera has high quantum efficiency and low dark current and is particularly sensitive for tissue imaging. It has been reported that common duct reflected spectra display a characteristic lipid peak at 930 nm and a strong water peak at 970 nm and that venous structures have absorption peaks at 760 nm (deoxyhemoglobin) and 800 nm (oxyhemoglobin). Including lipids and water as separate analytes improve detection accuracy since it is known that the concentration of these analytes in tumors is different from that in surrounding tissue. HSI is also capable of recognizing nerve fibers based on both spectral and spatial information of nerves and by using spectral angle mapping methods.

Accordingly, embodiments according to the invention can include an HSI system with both VNIR and SWIR cameras that can: i) covers broad range of spectra to image multiple biomarkers; ii) provide maximum tissue penetration using the infrared light, and iii) can detect not only cancer tissue but also vessels and nerve fibers, which may be useful for image-guided procedures where cancer tissue may need to be completely resected but vessels and nerves should be spared. HSI collects spectra from millions of pixels of a large field of view, and can provide rapid diagnosis for a large area.

A hypercube of data represents a full HSI image at one point in time. Spectral curves are obtained, each spectral curve associated with a pixel in a two-dimensional spatial image. In this application, the spectral curves represent optical properties of normal or cancerous tissue. For a two-dimensional image size, (e.g. 1004×1392 pixels) almost 1.4 million spectral curves are included in one hypercube. In some embodiments according to the invention, each spectral curve may include 425 data points resulting in the one hypercube containing about 600 million data points. The ability to extract important diagnostic information from such a large spectral dataset can enable a more complete exploration of the potential of hyperspectral imaging. In some embodiments according to the invention, the HIS system utilizes deep learning techniques, not previously explored to extract cancer spectral signatures from HSI hypercubes representing tissue samples from a large number of patients at the pixel-by-pixel level. These cancer spectral signatures may be used in a novel processing method to provide cancer detection during surgery.

FIGS. 1A-1F show various illustrative embodiments of HSI imaging apparatus. The invention is not limited by these embodiments as many other optical and hardware configurations may be conceived in practice of the general inventive concept. For example, in some embodiments more than two HSI cameras may be used. Referring to FIG. 1A, an illustrative embodiment of HSI imaging apparatus 100 is shown wherein a camera 101, having a first spectral sensitivity, and a camera 102, having a second spectral sensitivity, are attached to a mount 104. An object 105 is stationary while the mount 104 is controllably moved in the direction 109 with respect to the object to accomplish an image scan of the object. The object is, for example, an ex vivo tissue sample or in vivo tissue during surgery of a live patient. Camera 101, having field of view 107, and camera 102, with field of view 106, are attached at fixed angles, Θ1 and Θ2, with respect to the vertical 50 so that their fields of view overlap at the object surface. An illuminator 103 can be attached to mount 104 and illuminates across a field of illumination 108 such that the spectral irradiance is nearly uniform across the object surface within the fields of view 106 and 107. The object distance 113 from the lenses of the cameras may be generally fixed during a scan and the lenses of the cameras are spaced at a distance 114 to overlap the fields of view at the surface if required. The focal length of the cameras may vary. The first spectral sensitivity may overlap with the second spectral sensitivity, for example, in a preferred embodiment the first spectral sensitivity is 400 nm-1000 nm and the second spectral sensitivity is 900 nm-1700 nm. In the embodiment of HSI imaging apparatus 100, a hyperspectral image of a particular area of object 105 is taken from both of cameras 101 and 102 at the same time and combined to create a single hypercube of data.

Figure 1B:
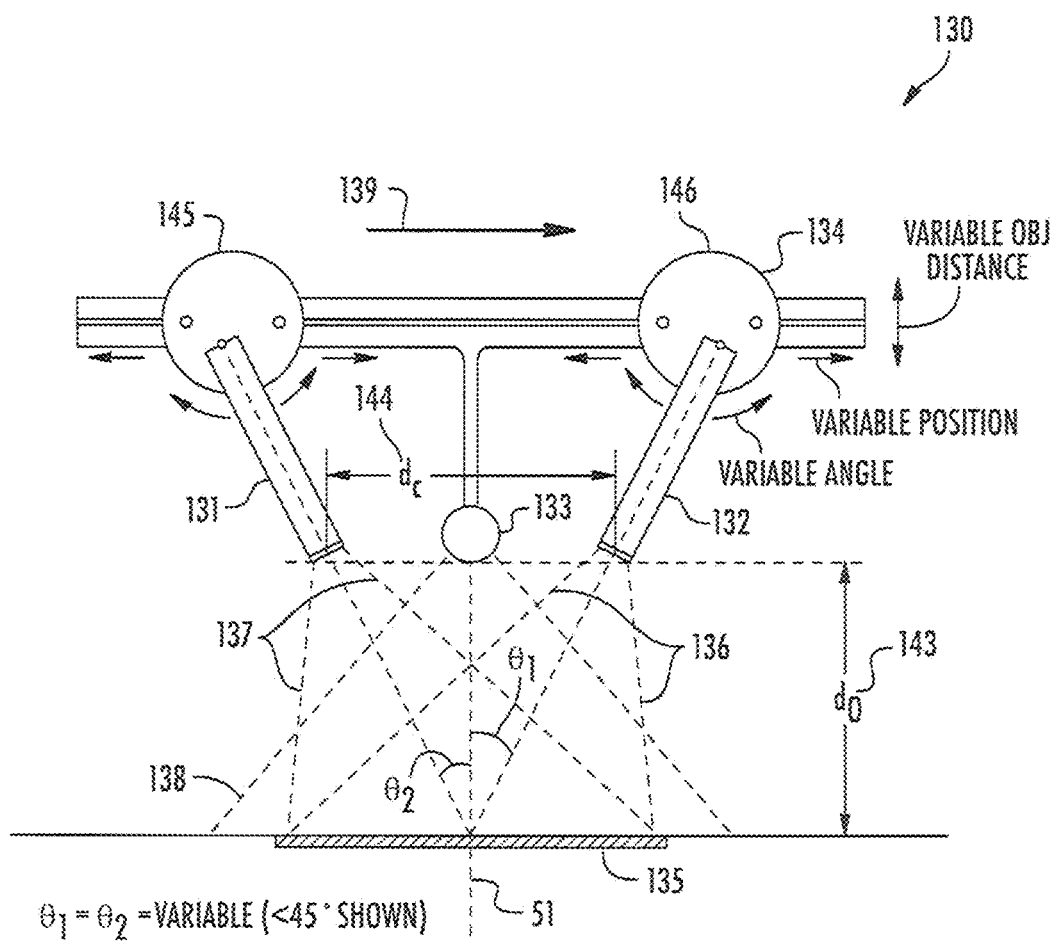
FIG. 1B is a schematic drawing of a hyperspectral imaging system in some embodiments according to the invention as viewed from one side. The system can include two hyperspectral imaging cameras, one for the visible and near infrared camera and the other one for the short-wave infrared. The two hyperspectral imaging cameras are mounted on the frame and may be controlled by a processor circuit coupled to a mechanical system for image scanning. The two hyperspectral imaging cameras are placed at different angles and the angles can be adjusted as shown in the graph. The two hyperspectral imaging cameras can moved along the scanning direction and the distance between the two hyperspectral imaging cameras is adjustable. The height between the cameras and the sample can also be adjusted. The field of views of the two hyperspectral imaging cameras are overlapped at the region of interest that can be tissue samples or objects. The light illumination is located at the center for illuminating the samples or objects.
Figure 1C:
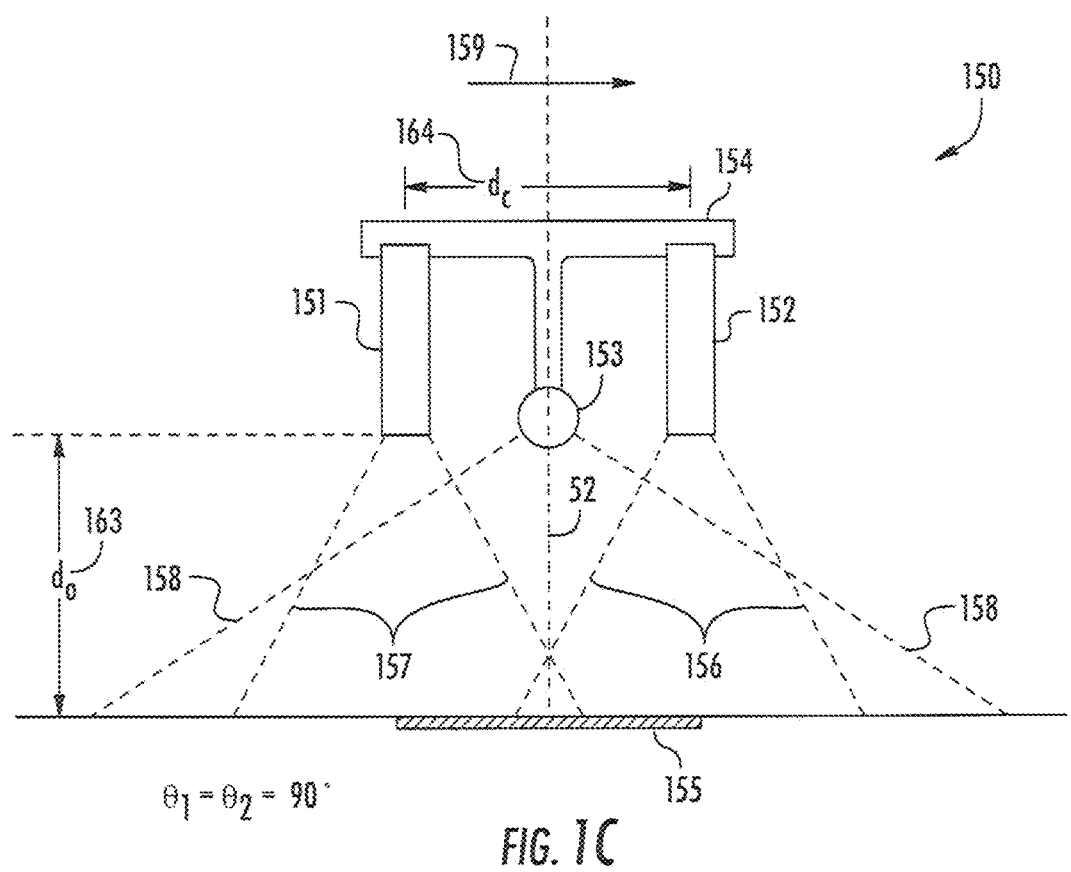
FIG. 1C is a schematic drawing of a hyperspectral imaging system in some embodiments according to the invention as viewed from one side. The system can include two hyperspectral imaging cameras, one for the visible and near infrared camera and the other one for the short-wave infrared. The two hyperspectral imaging cameras are mounted on the frame and can move along the same direction at the same time for image scanning. The height between the hyperspectral imaging cameras and the sample can also be adjusted. The light illumination is located at the center for illuminating the samples or objects.
Figure 1D:
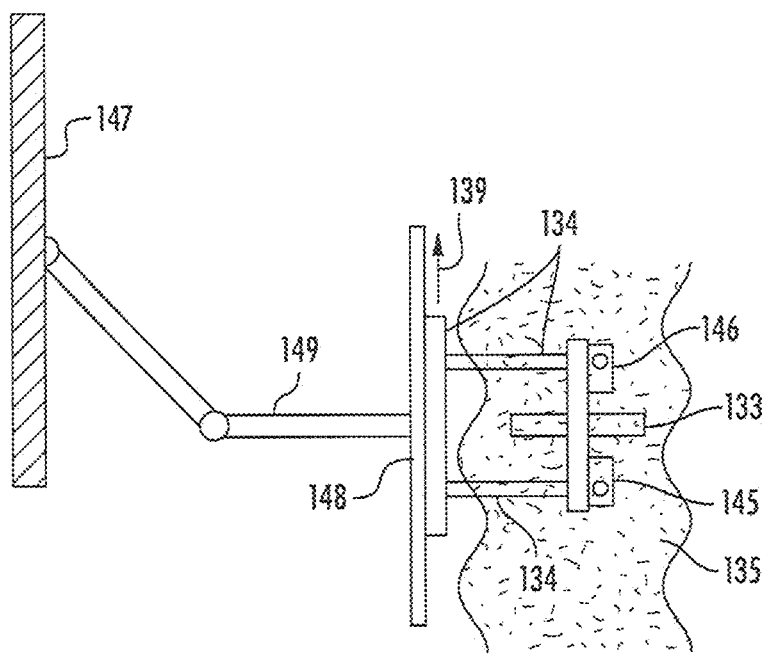
FIG. 1D is a schematic drawing showing the top view of the hyperspectral imaging system in some embodiments according to the invention. The hyperspectral imaging cameras are mounted on a frame and can move along the frame for imaging scanning. The illumination system can also be fixed to the frame and can also move along the frame during the scanning. The whole imaging system may also be mounted to a supporting system, such as a cart or a wall.
Figure 1E:
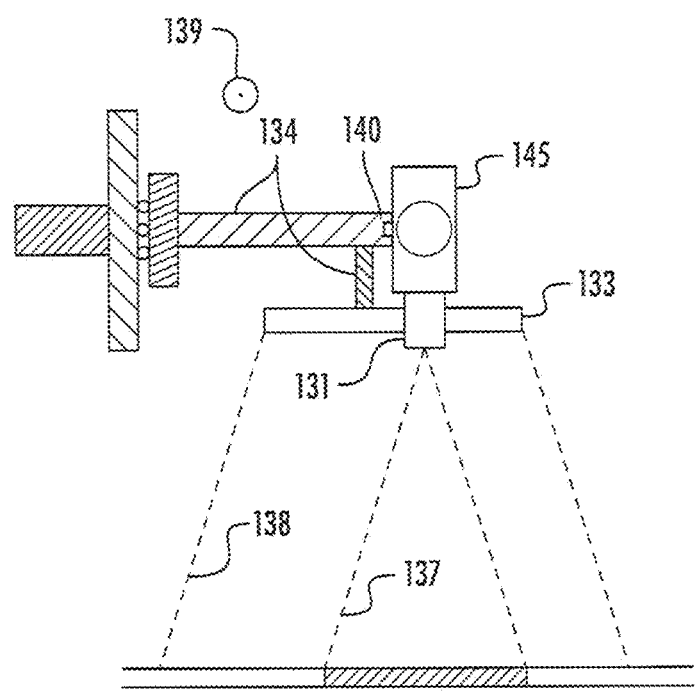
FIG. 1E is a schematic drawing showing an end view of the hyperspectral imaging system in some embodiments according to the invention. The two hyperspectral imaging cameras and the illumination system are mounted to the frame. The two hyperspectral imaging cameras can take images from of object that is under the cameras and is illuminated by the illumination lights. The whole frame can move along different directions for scanning the object.
Figure 1F:
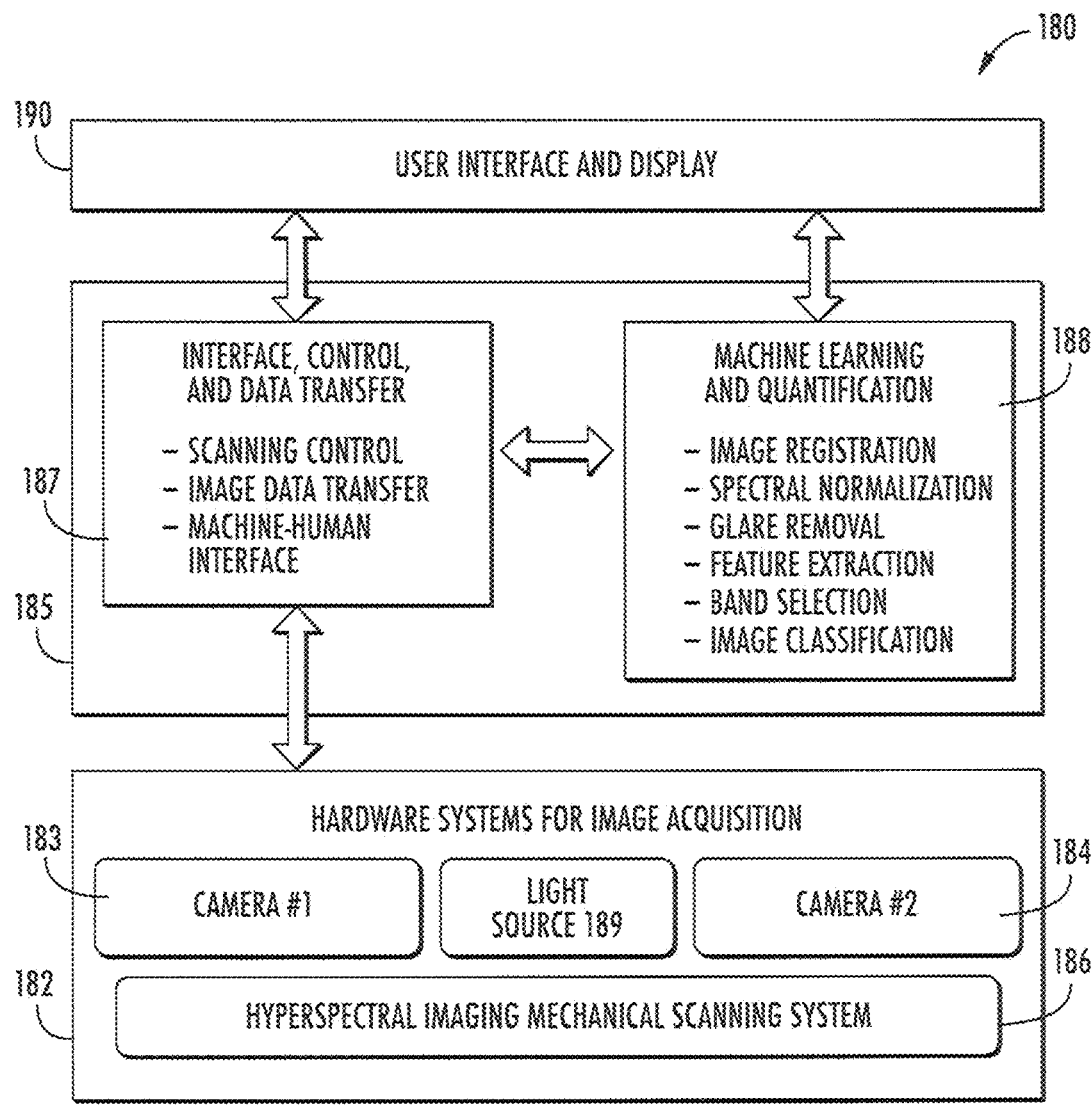
FIG. 1F is a block diagram of a HSI system in some embodiments according to the invention including the following components: i) The acquisition scanning platform, which is composed by two HSI cameras and illumination system; ii) The hyperspectral data processing unit that includes the core software for managing all the subsystems; iii) The processing software platform, where the HSI processing tools and classification algorithms are implemented; and iv) The user interface, where the operator controls the interface of the system.

Referring to FIGS. 1B, 1D and 1F, another illustrative embodiment of HSI imaging apparatus 130 is shown wherein a camera 131, having a first spectral sensitivity, and a camera 132, having a second spectral sensitivity, are attached to a translatable mount 134. An object 135 is stationary while the mount 134 is controllably moved in the direction 139 with respect to the object to accomplish an image scan of the object. The object is, for example, an ex vivo tissue sample or in vivo tissue during surgery of a live patient. Camera 131 is attached to mount 134 by camera mount 145 and camera 132 is attached to mount 134 by camera mount 146. Camera mounts 145 and 146 are translatable and rotatable with respect to mount 134. Camera 131, having field of view 137, and camera 132, with field of view 136, are attached at variable angles, Θ1 and Θ2, with respect to the vertical 51 so that their fields of view can overlap at the object surface. An illuminator 133 is attached to mount 134 and illuminates across a field of illumination 138 such that the spectral irradiance may be uniform across the object surface within the fields of view 136 and 137. The object distance 143 from the lenses of the cameras may be generally fixed during a scan and the lenses of the cameras are spaced at a distance 144 to attain overlap of the fields of view at the surface if required. The focal length of the cameras may vary and the spectral sensitivities of each camera have the same characteristics as in HSI imaging apparatus 100. In the embodiment of HSI imaging apparatus 130, a hyperspectral image of a particular area of object 135 is taken from both of cameras 131 and 132 at the same time and combined to create a single hypercube of data.

Referring to FIG. 1C, another illustrative embodiment of HSI imaging apparatus 150 is shown wherein a camera 151, having a first spectral sensitivity, and a camera 152, having a second spectral sensitivity, are attached to a translatable mount 154. An object 155 is stationary while the mount 154 is controllably moved in the direction 159 with respect to the object to accomplish an image scan of the object. The object is, for example, an ex vivo tissue sample or in vivo tissue during surgery of a live patient. Camera 151, having field of view 157, and camera 152, with field of view 156, are attached with optical axes parallel to the vertical 52 so that their fields of view do not overlap at the object surface. An illuminator 153 is attached to mount 154 and illuminates across a field of illumination 158 such that the spectral irradiance is nearly uniform across the object surface within the fields of view 156 and 157. The object distance 163 from the lenses of the cameras is generally fixed during a scan and the lenses of the cameras are spaced at a distance 164 to attain overlap of the fields of view at the surface as required. The focal length of the cameras may vary and the spectral sensitivities of each camera have the same characteristics as in HSI imaging apparatus 100. In the embodiment of HSI imaging apparatus 150, a first HSI image of a particular area of object 155 is taken by camera 151 at a first time and a second HSI image taken of the same particular are by camera 152 at a second time. The first HSI image and the second HSI image are combined by a processor circuit to create a hypercube of data that can include the spectral data included in both the first and second HSI images, which are comprised of first and second hyperspectral image data, respectively.

Referring to FIG. 1F, a block diagram of an illustrative embodiment of an HSI system 180 is shown. HSI system 180 includes hardware systems 182 for image acquisition which includes a light source 189 and at least two cameras, camera 183 and camera 184 and a mechanical scanning system 186 to which the cameras and light source are attached. Hardware system 182 may be configured, for example, as any of the illustrative embodiments of FIGS. 1A-1E. As described herein, in some embodiments, more than two cameras may be employed to extend the spectral range of the hypercube. HSI imaging apparatus 182 is communicatively connected to an HSI processor 185, which is also referred to herein as a processor circuit and is described in further detail with reference to FIGS. 9 and 10.

HSI processor 185 is configured with a first logic block 187 to receive and process images from hardware system 182, to control mechanical scanning system 186 and to drive a user interface and display 190. HSI processor 185 is further configured to with a second logic block 188 for image processing that performs tasks including image registration, spectral renormalization, glare removal, feature extraction and band selection, image classification and machine learning algorithms for producing a diagnostic 2D image of an object area. The diagnostic 2D image, which is displayed via the user interface and display 186, indicates, on a display screen, regions of cancerous tissue superimposed upon a traditional RGB image of the object area. In a preferred embodiment, user interface and display 186 is available to be used and observed by a surgeon during surgery.

The HSI cameras can be a micro-Hyperspec VNIR and a micro-Hyperspec SWIR cameras (HeadWall Photonics, MA). Other HSI capable cameras may also be used in some embodiments. The visible and near-infrared (NVIR) camera can have a spectral range of 400-1000 nm. The lens used in this camera can be a Xenoplan 1.9 with 35 mm of focal length and a broadband coating for the spectral range of 400-1000 nm. The shortwave infrared (SWIR) camera can have a spectral range of 900-1700 nm, and can include an Indium Gallium Arsenide (InGaAs) detector array. Both cameras can use a pushbroom scan to capture both spectral and spatial dimensions. In some embodiments according to the invention, the cameras can be other types of cameras using other scanning mechanisms, such as a snapshot camera using a snapshot scanning mechanism or a Snapscan camera using a Snapscan scanning mechanism.

Figure 2:
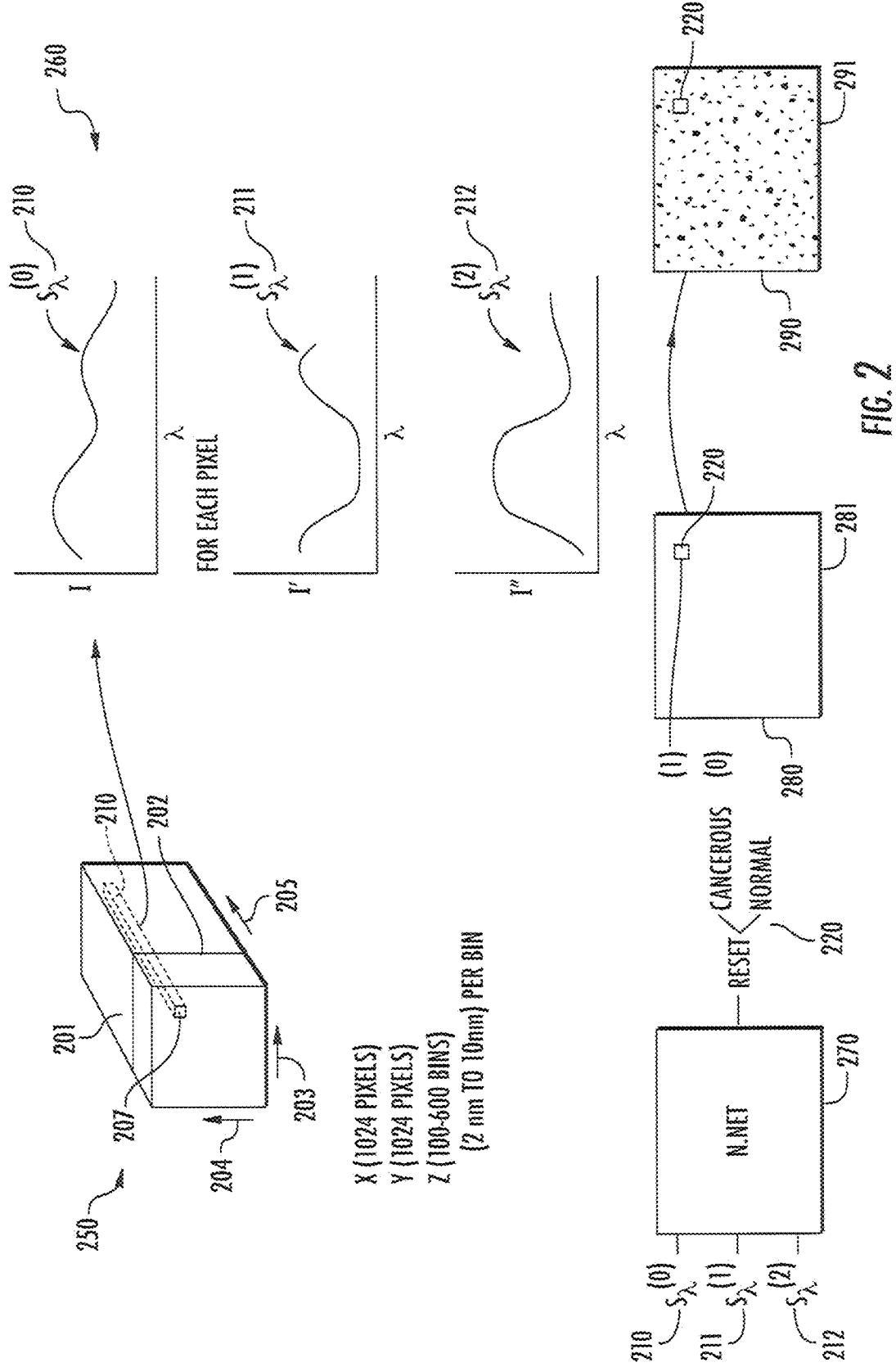
FIG. 2 is a visual flow diagram showing the processing pipeline of the hyperspectral image data in an illustrative embodiment of the invention. The hyperspectral image data can be three-dimensional (3D) data with two dimensions for the spatial information (x, y) and one dimension for the spectral information ($\lambda$) at each pixel. The 3D data will then be processed with numerical processing such as the first derivative, the second derivative, and etc. The original data and the processed data are then input into the processing pipeline that includes pre-processing, normalization, trained neural networks, and etc. The output of the processing pipeline is the classification of the hyperspectral image into cancer or normal tissue. The cancer tissue can be further classified into different types of cancers. The classification results and maps will be displayed and overlaid with the original images.

Referring to FIG. 2, a method 200 for processing a hypercube 201 is shown in a series of operations, which can be performed using the processor circuit 180. Beginning with operation 250, a hypercube 201 including HSI image data from an HSI camera is measured for an object along with an RGB image of the object. Hypercube 201 contains a set of pixels in spectral planes 202 (along the z-axis) wherein the set of pixels are located in the 2D spatial axis 203 (x) and spatial axis 204 (y), respectively. The z-axis 205 represents reflected spectral flux measured from an x, y position of an object, integrated over a small spectral range (2 nm to 6 nm). A spectral profile 210, $S\lambda(0)$, for a given pixel 207 is processed as shown in the remaining diagrams. A set of spectral profiles for the entire hypercube 201 is processed in parallel in a similar way to spectral profile 210.

At operation 260 the hypercube is processed further wherein spectral profile 210, $Sk(0)$, is differentiated at least twice to obtain a first derivative spectral profile 211, $Sk(1)$, and a second derivative spectral profile 212, $S\lambda(2)$. Although the spectral profiles are shown as graphical output, this format is used for the purposes of illustration and it will be understood that the spectral profiles may be processed as data structures or as functions expressing spectral intensity (in spectral profile 210) as a function of wavelength.

At operation 270, the spectral profiles 210, 211 and 212 are input into a machine learning algorithm 215 (for example, an artificial neural network) which processes the profiles to produce a single result 220 for the given pixel 207. In some embodiments, the result pixel 220 is a binary result indicating if the spatial location of the object corresponding to the given pixel 207 is cancerous (1) or normal (0). In other embodiments, fuzzy logic may be used to create multiple levels of diagnosis for the result pixel, for example, cancerous with high probability (3), likely cancerous (2), possibly cancerous (1), not cancerous (0).

In some embodiments according to the invention, the artificial neural network can a convolutional neural network (CNN) used to classify cancerous and normal tissues at the cancer margin. Due to the uniqueness of HSI data, the inception-v4 CNN architecture can customized in several ways to optimize the CNN to hypercube data in image-patches that are 25×25×C, where C is the number of spectral bands of each HSI camera. A suitable CNN can be provided using TensorFlow on an Ubuntu machine running NVIDIA Titan-XP GPUs. The early convolutional layers may be modified to handle the selected patch-size and create smaller inception blocks that allow for faster training and classification using the CNN. Training can be performed, for example, up to 50 epochs, where one epoch of training data may run for about 1 hour using HSI; and deployment of the fully-trained CNN on a single GPU to classify a new HSI scene with hundreds of patches may requires only 25±10 seconds and can be improved to achieve real time. As used herein, the term "real time" as it relates to the performance of a system, is one in which input data is processed within milliseconds so that the processed data is available virtually immediately as feedback.

At operation 280, the result pixel 220 is expressed as a single pixel in a 2D diagnostic overlay image of the object area at a location corresponding to the spatial x and y positions of the given pixel 207. All of the spectral profiles in hypercube 201 are processed according to operations 260, 270 and 280 to create a 2D diagnostic overlay image 281 of the object.

At operation 290, diagnostic overlay image 281, containing result pixel 220, is overlaid with the RGB image of the object area and displayed as a single 2D diagnostic image 291 of the object area. In one embodiment wherein the pixel results are binary, a pixel indicating non-cancerous diagnosis may be a fully transparent to the overlaid image and a cancerous a pixel indicating a cancerous diagnosis may be non-transparently overlaid as a specific color(s), for example red.

Figure 3:
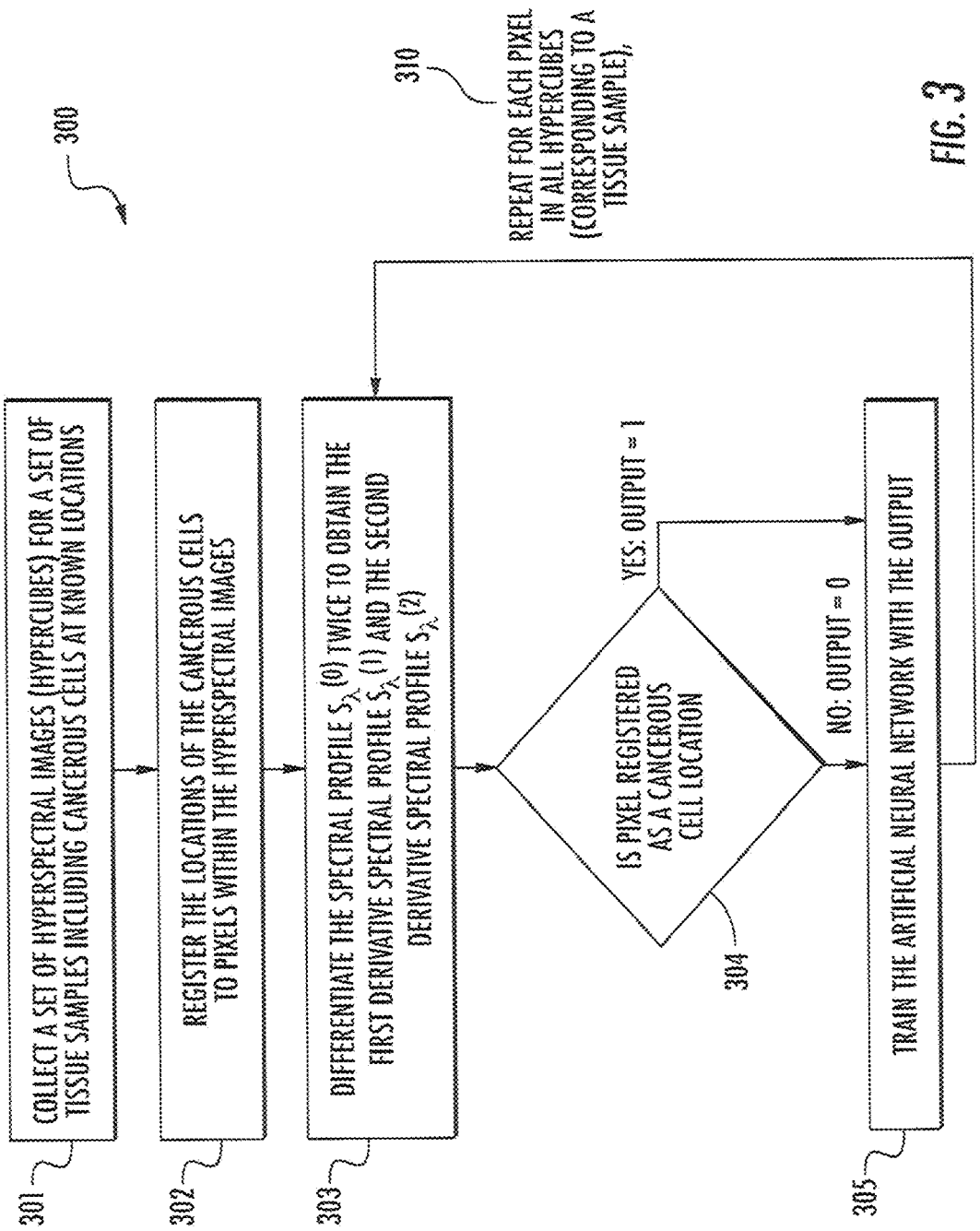
FIG. 3 is a block diagram of the training operations of a neural network in an illustrative embodiment of the invention including: 1) Collect the hyperspectral images with known cancer tissue and normal tissue; 2) Detect and map the cancer tissue with known locations on the hyperspectral images; 3) For each pixel or a group of pixels in the hyperspectral image, process the original data and obtain the secondary information such as the first derivative, the second derivative, and etc. The original data, the derived data, and the known location information of the caner tissue are input into the neural networks for the training process; and 4) Repeat the above steps and validate the neural networks for all the data in the 3D hyperspectral images.

FIG. 3 is a flow diagram of method 300 for training an artificial neural network to classify cancerous tissue for a pixel image area in an HSI image. At operation 301, a set of hyperspectral images of a set of tissue samples are taken wherein the set of tissue samples are known to contain cancerous cells at various locations. The locations of the cancerous cells are known and, at operation 302, the cancerous cell locations are registered for each pixel image location in the set of hyperspectral images.

At operation 303, a measured spectral profile $S\lambda(0)$ for a pixel is differentiated twice to obtain a measured first derivative spectral profile $S\lambda(1)$ and a measured second derivative spectral profile $S\lambda(2)$. At operation 304, if the pixel location is registered to be cancerous, then the output of the neural network, which is a single binary number, is programmed to be a 1. If the pixel location is registered to be non-cancerous, then the output of the neural network is programmed to be 0. At operation 305, the artificial neural network including all internal weighting coefficients are trained using $S\lambda(0)$, $S\lambda(1)$ and $S\lambda(2)$ as the inputs.

Then, at operation 310, operations 303, 304 and 305 are repeated for each pixel in each hyperspectral image for the set of tissue samples to complete the training of the artificial neural network.

Figure 4:
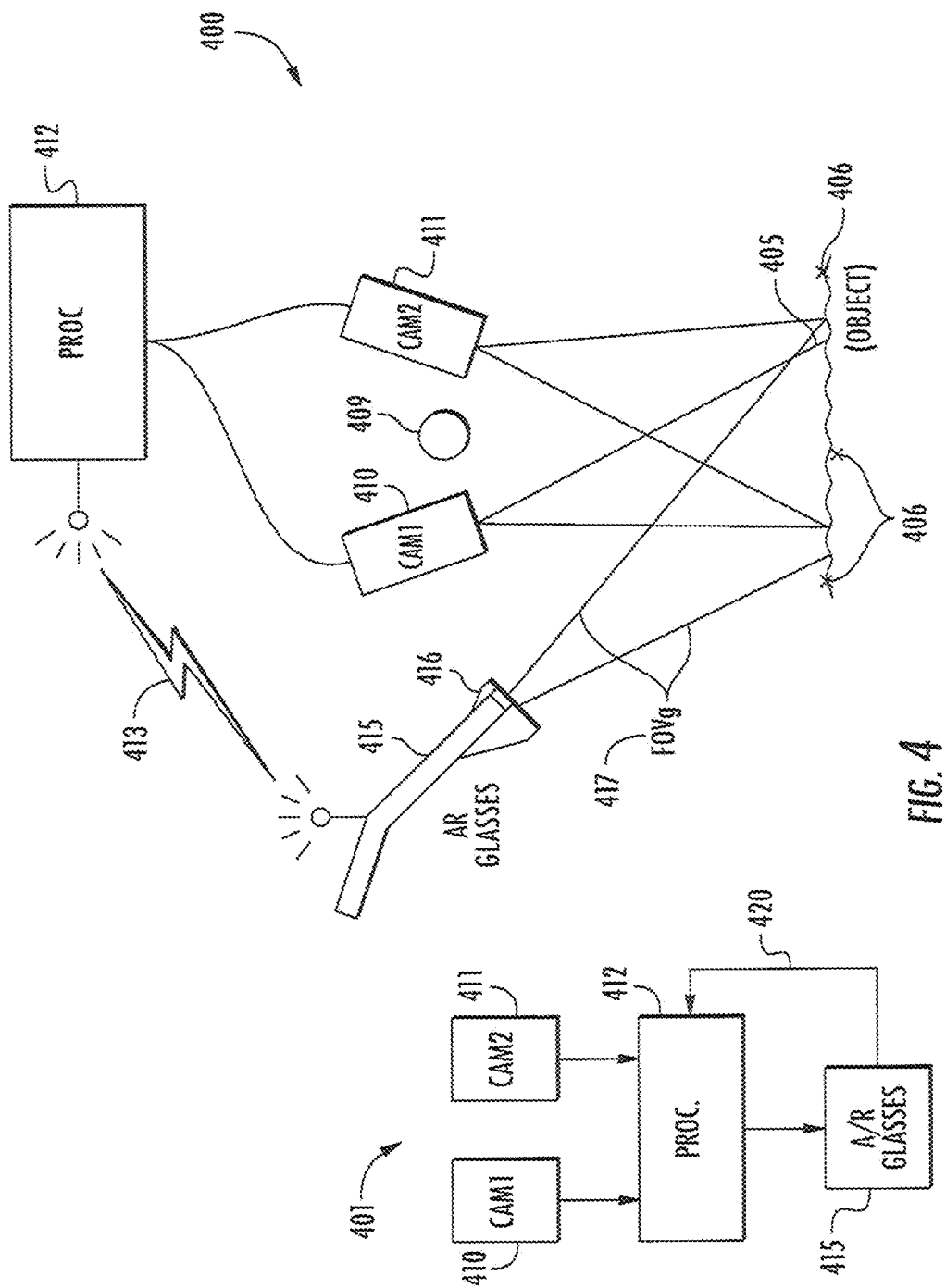
FIG. 4 is a schematic illustration of an augmented reality and visualization hyperspectral imaging system in some embodiments according to the invention. The hyperspectral image data is processed to classify the cancer and normal tissue on the image. The classification map of the cancer tissue is then mapped into the original hyperspectral image in order to inform the clinician of the location of the cancer tissue. The clinician may wear an augmented reality glass and the classification map of the cancer tissue is projected into the glass and overlaid with the original hyperspectral images. The transfer of the classification map can be transmitted via a wireless system from the computer workstation to the augmented reality glass.
Figure 5:
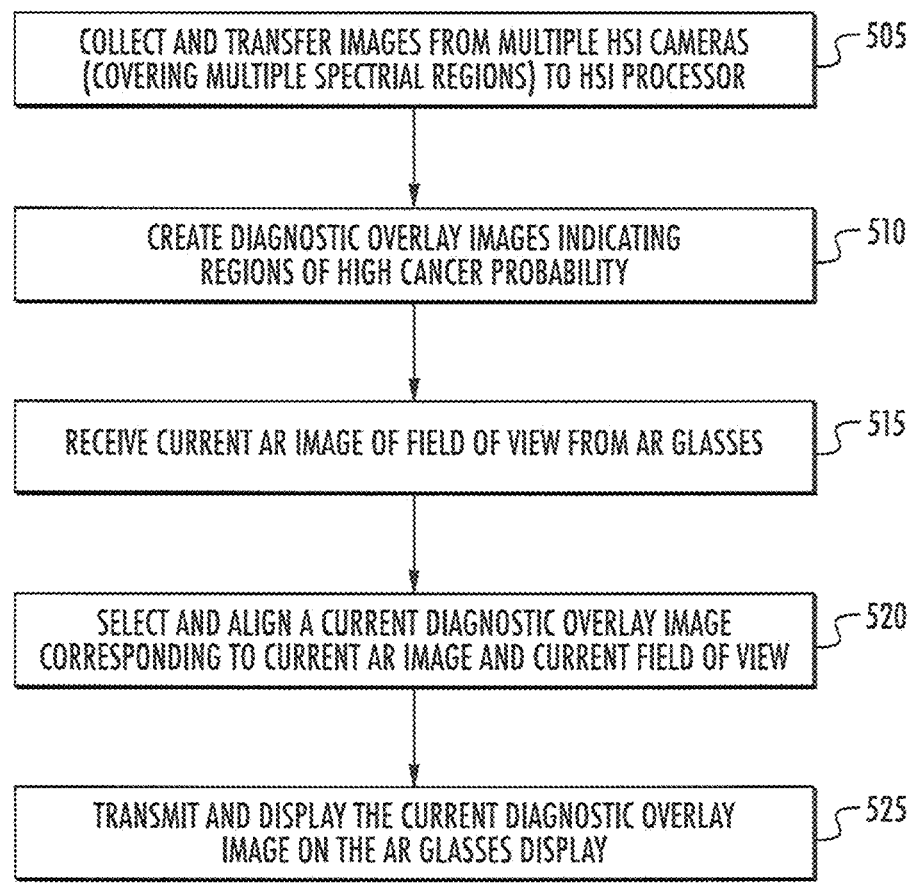
FIG. 5 is a flowchart illustrating methods of displaying of the classified cancer tissue through the augmented reality system in some embodiments according to the invention. Top: The original hyperspectral image with some fiducial markers that are used for the registration between the real-time images and the classification map. Bottom: The overlay of the classification map and the original hyperspectral images. The tumor location is mapped to the original hyperspectral image to help the clinician to identify the cancer tissue.

In another embodiment, an apparatus for augmented reality based surgical operations is conceived according to the diagrams of FIGS. 4 and 5. Referring to FIG. 4, an illuminator 409 illuminates an object 405 (for example, a tissue sample or live tissue). Two hyperspectral imaging cameras, HSI camera 410 and HSI camera 411, are communicatively connected to an HSI processor circuit 412. A pair of augmented reality glasses 415 are communicatively connected (link 413) to HSI processor circuit 412 so as to enable the transmission and reception of 2D digital images therefrom. Communications link 413 is a wireless transmission link in a preferred embodiment.

Augmented reality glasses, as known in the art, are configured with a display that overlays digitally stored (or real-time communicated images) semi-transparently over the wearer's field of view to incorporate a digital image into the wearer's perception of real objects as seen through the augmented reality glasses. In some embodiments, augmented reality glasses 415 (sometimes referred to as the head mounted AR system) are eyeglasses or other head mounted system worn by, for example, a surgeon, which detects, via an onboard optical camera 416, images 420 of object 405 in field of view 417 of the surgeon during examination. Object 405 includes fiducial marks 406 which are also imaged by onboard camera 416 in field of view 417. In some embodiments, images 420 are transferred to HSI processor circuit 412 for determining the position of field of view 417 in real-time.

Referring to FIG. 5, a method 500 for using the apparatus 400 is described. Method 500 begins at operation 505 when HSI images are transferred, from HSI camera 410 and HSI camera 411 to HSI processor circuit 412 for one or more object locations. HSI processor circuit 412 is configured to record the HSI images of the object and process them. At operation 510, the HSI images of the object are processed by an HSI processor circuit 412 to create diagnostic overlay images for the one or more object locations, wherein, the diagnostic overlay images indicate regions (pixels) of high probability of cancerous tissue. In an embodiment of the invention, the diagnostic overlay images are created as taught in this disclosure, for example in FIG. 2 and method 200. In other embodiments other post processing methods for HSI images may be used, for example, spectral-spatial classification methods based on the selected features from the hyperspectral cubes.

At operation 515, a current AR image from the onboard camera of the augmented reality glasses are received by the HSI processor. At operation 520, a current diagnostic overlay image for an object location is selected and aligned based on the position of the fiducial marks of the current AR image.

At operation 525 the current diagnostic overlay image is transmitted to the AR glasses and displayed on the AR glasses for the surgeon to see during examination and operation.

Figure 6A:
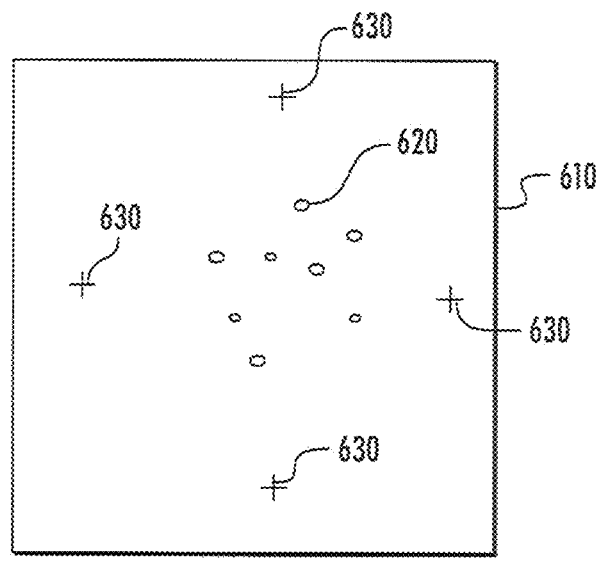
FIGS. 6A and 6B are diagrams of images showing the field of view with and without, respectively, an augmented display of the diagnostic overlay image indicating cancerous tissue areas in some embodiments according to the invention.
Figure 6B:
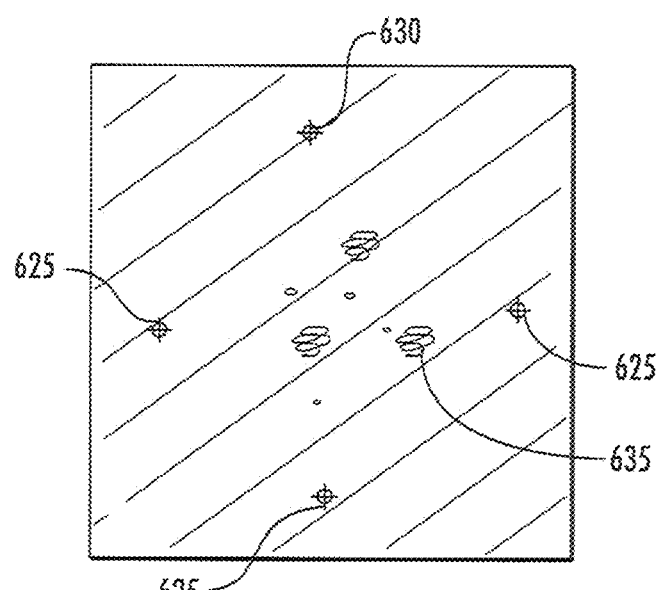

In FIG. 6A, a field of view 610 is shown for an area of operation showing various features of tissue 620 in the field of view and a set of fiducial marks 630 shown as crosses. In FIG. 6A, the AR glasses are not displaying a diagnostic overlay image. In FIG. 6B, field of view 615 includes fiducial alignment marks 625, shown as circles. Field of view 615 corresponds to field of view 610 in FIG. 6A, but for which a diagnostic overlay image is displayed by the AR glasses display indicating regions 635 of high probability of the presence of cancerous tissue, for example, as bright red pixels.

The AR system composed of three different components: localization, calibration, and tracking (sometimes referred to as registration and tracking). In the localization phase, the HoloLens AR headset (Microsoft, Redmond, Wash., USA) utilizes SLAM to generate a spatial mesh of the environment to establish collision detection and attempts to find the object and the tracking target. Once the position of the targets is determined, a calibration hologram is anchored to the object in a predetermined location, centered on the phantom and floating 0.1 mm above it. The user is then guided through several steps to make small adjustments to the tilt and position of the holograms to account for the imperfections caused by headset orientation. Auxiliary markers and a holographic axis make the alignment process much easier. After calibration, the targets are ready to be tracked and the menus for the various options for hologram manipulations is displayed. During tracking, the movements of the head mounted AR system are determined in real-time as well as the "pose" or view point that generates the field of view 417 seen from the perspective of the onboard optical camera 416. Accordingly, in operation the HIS system can track the movement of the head mounted AR system within the environment (as well as the field of view 417) and can provide updated HSI spectral image data to the HSI processor for generation of the diagnostic overlay, which can in-turn be provided to the head mounted AR system to augment the display thereon of the video seen by the user. As described herein, this feedback loop can be achieved in real-time or in near real-time to enable the user to perform, for example, a surgical procedure on a patient using the HSI system in some embodiments according to the invention.

Figure 7:
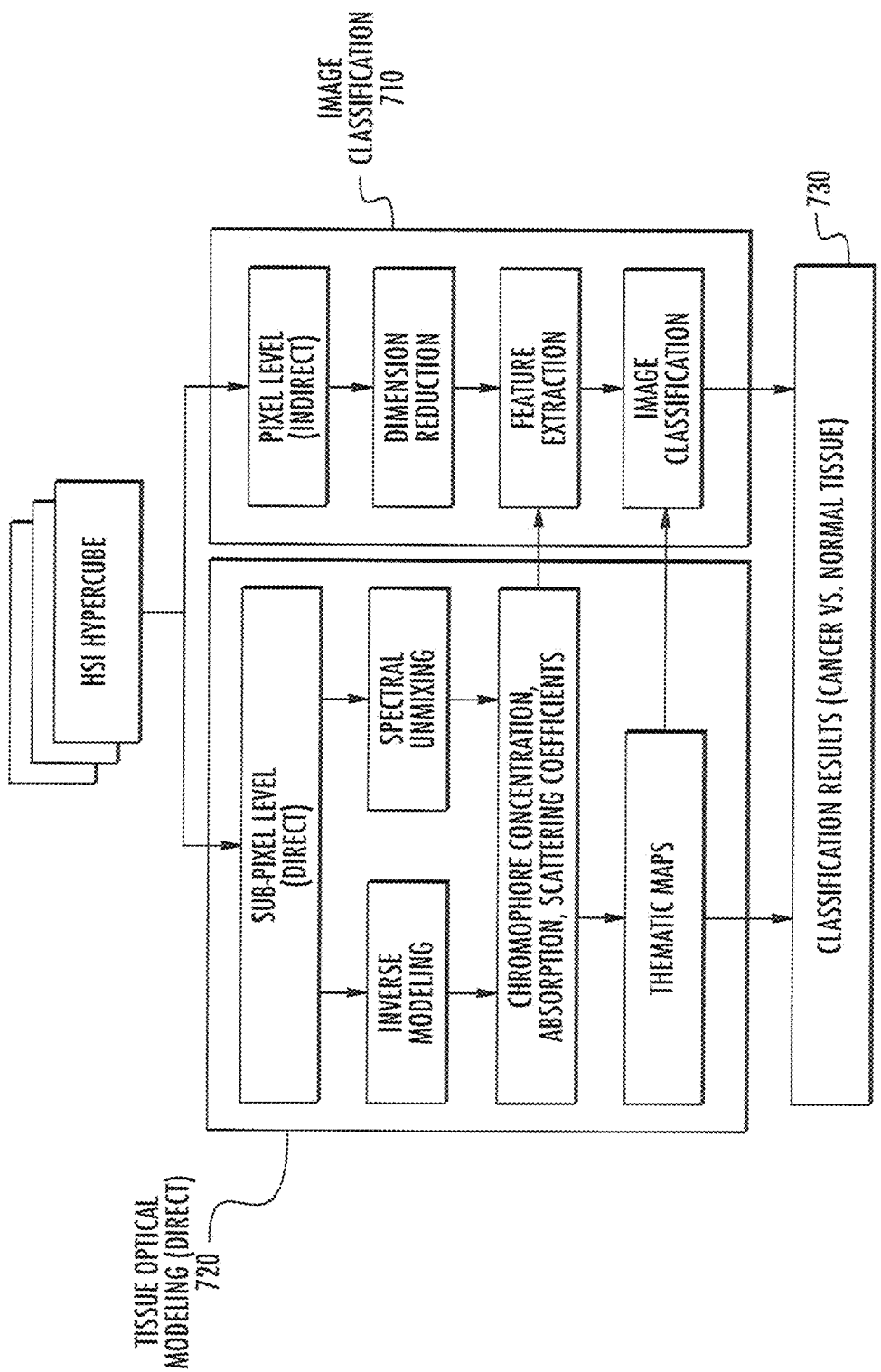
FIG. 7 is a block diagram showing an overview of the spectral modeling and quantification method in some embodiments according to the invention. The approach can include: 1) the spectral un-mixing and modeling methods, a direct approach that measures physiological parameters, as shown on the left side with green boxes; and 2) Image classification methods, an indirect technique as shown on the right with blue boxes, which can generate a cancer probability map. The combined modeling methods with image classification and un-mixing methods link spectral signatures with tissue pathology in some embodiments according to the invention.
Figure 8:
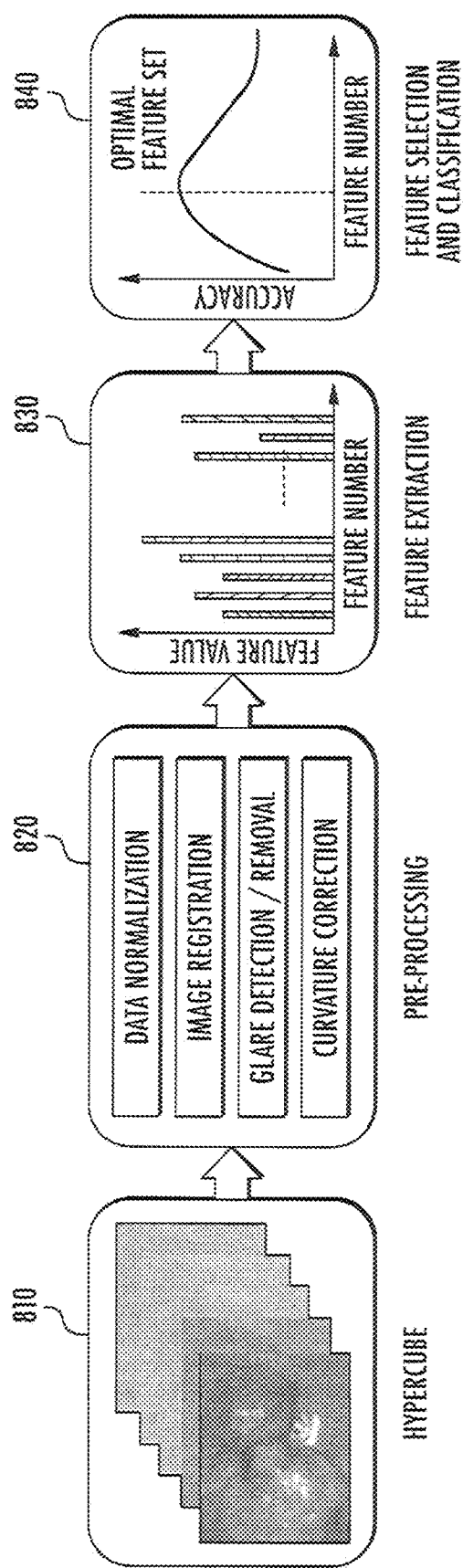
FIG. 8 is a block diagram indicating HSI data processing and quantification operations in some embodiments according to the invention. HSI data are pre-processed by spectral normalization, image registration, glare detection, and curvature correction. Image features are then extracted from the HSI data, and a discriminative feature set is selected and used for the classification of cancer and benign tissue.

In relation to HSI processor, second logic block 188 of FIG. 1F is further explained. FIG. 7, the tissue optical modeling 720) and hyperspectral image classification methods 710 are combined for cancer detection. Image classification methods 710, shown at the right panel, is an indirect way to link the physiological features with disease states. The spectral unmixing and inverse modeling methods are direct ways, as shown at the left panel (tissue optical modeling methods 720). Image classification can generate probability maps that depict pathological status of the tissue, which would enable the in vivo detection and grading of a pathology. Spectral unmixing can decompose the spectrum of each pixel into a collection of constituent spectra and corresponding abundances. The tissue optical modeling methods 720 have been combined with the image classification methods 710 in order to link between the spectral content of the acquired images and the classification results 730 status (cancerous or non-cancerous) of the examined sample In FIG. 8, further description for the pipeline of the hyperspectral image processing of hypercube 810 by the HSI processor is shown in three major operations: Pre-processing operation 820, Feature Extraction Operation 830 and Feature Selection Operation 840. Pre-processing operation 820 includes the pre-processing operations of data normalization, image registration between images acquired at different time points or from different cameras, glare detection and removal processing, and curvature correction. Feature extraction operation 830 extracts the spatial-spectral features from the hyperspectral image data for the representation of the different types of tissues. Feature selection operation 840 selects the optimal features from the feature sets and then use the optimal features within spectral profiles for image classification of cancer and normal tissues.

Because embodiments according to the invention may be implemented using software instructions, the components and operation of a generic programmable computer system on which various embodiments of the disclosed technology may be employed will first be described. The components and operation of a computer network having a host or processor circuit and one or more remote or servant computers therefore will be described with reference to FIG. 9. This operating environment is only one example of a suitable operating environment, however, and is not intended to suggest any limitation as to the scope of use or functionality of the disclosed technology.

Figure 9:
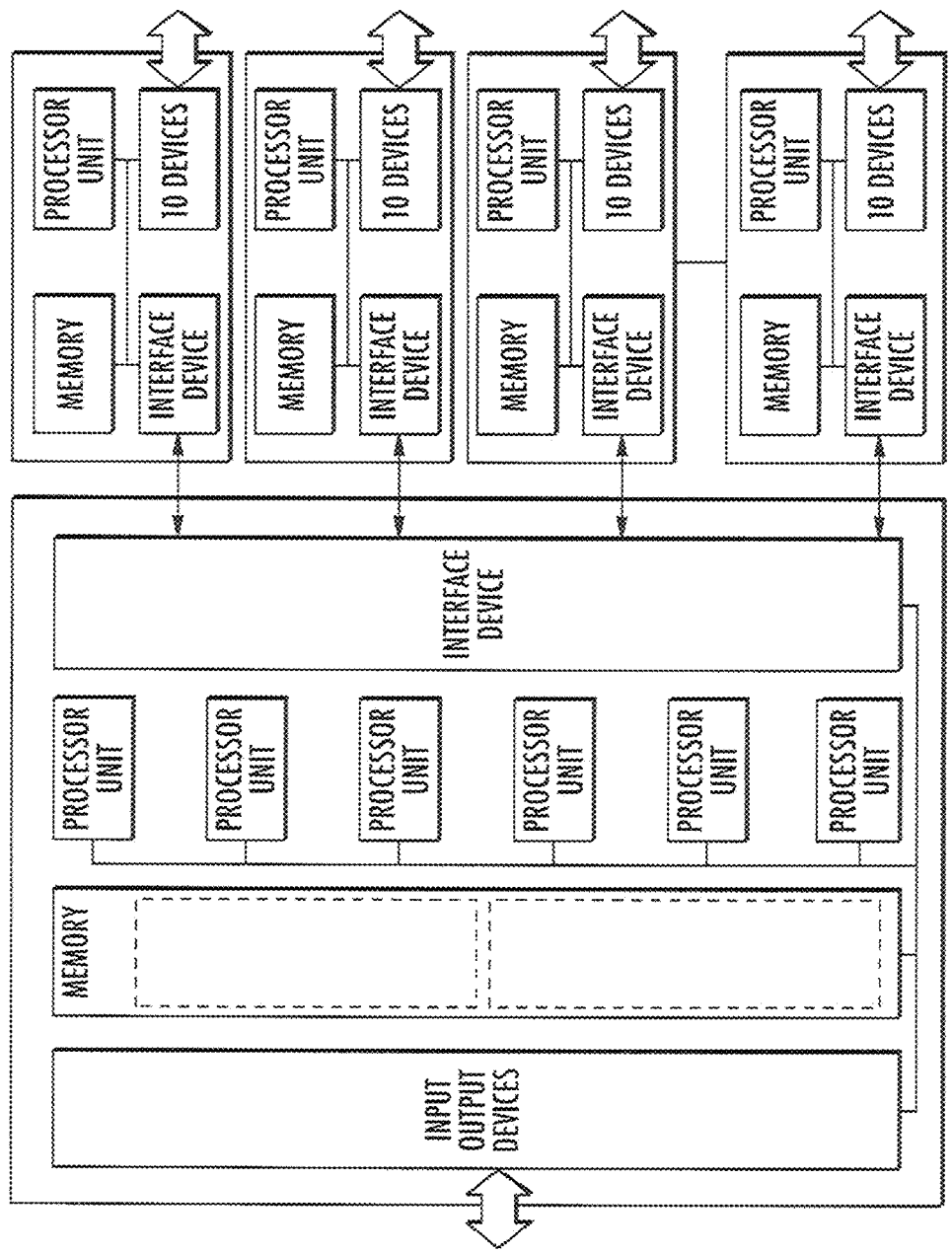
FIG. 9 is a block diagram of a processor circuit and associated co-processors that may be used to perform software operations of the HSI systems described herein, including real-time operations of an HSI system as part of an augmented reality system that provides real-time AR imaging in support of surgical intervention in some embodiments according to the invention.

In FIG. 9, the computer network includes a processor circuit. In the illustrated example, the processor circuit is a multi-processor computer that includes a plurality of input and output devices 105 and a memory. The input and output devices may include any device for receiving input data from or providing output data to a user. The input devices may include, for example, a keyboard, microphone, scanner or pointing device for receiving input from a user. The output devices may then include a display monitor, speaker, printer or tactile feedback device. These devices and their connections are well known in the art, and thus will not be discussed at length here.

The memory may similarly be implemented using any combination of computer readable media that can be accessed by the processor circuit. The computer readable media may include, for example, microcircuit memory devices such as read-write memory (RAM), read-only memory (ROM), electronically erasable and programmable read-only memory (EEPROM) or flash memory microcircuit devices, CD-ROM disks, digital video disks (DVD), or other optical storage devices. The computer readable media may also include magnetic cassettes, magnetic tapes, magnetic disks or other magnetic storage devices, punched media, holographic storage devices, or any other medium that can be used to store desired information.

As will be discussed in detail below, the processor circuit runs a software application for performing one or more operations according to various examples of the disclosed technology. Accordingly, the memory stores software instructions that, when executed, will implement a software application for performing one or more operations. The memory also stores data to be used with the software application. In the illustrated embodiment, the data contains process data that the software application uses to perform the operations, at least some of which may be parallel.

The processor circuit also includes a plurality of processor units and an interface device. The processor units may be any type of processor device that can be programmed to execute the software instructions, but will conventionally be a microprocessor device. For example, one or more of the processor units may be a commercially generic programmable microprocessor, such as Intel. Pentium. or Xeon microprocessors, Advanced Micro Devices Athlon™ microprocessors or Motorola 68K/Coldfire microprocessors. Alternately or additionally, one or more of the processor units may be a custom-manufactured processor, such as a microprocessor designed to optimally perform specific types of mathematical operations. The interface device, the processor units, the memory and the input/output devices are connected together by a bus.

Figure 10:
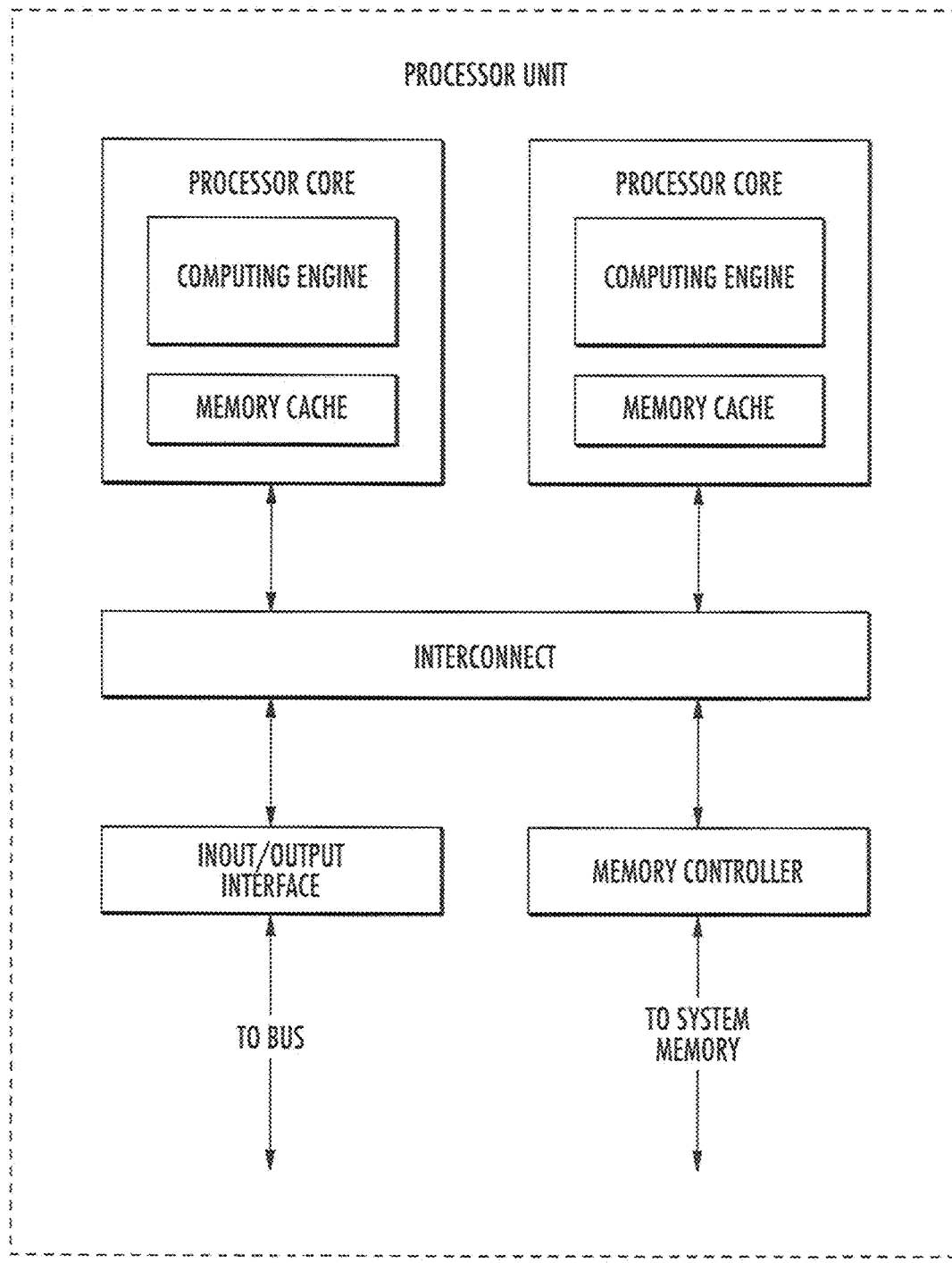
FIG. 10 is a block diagram of a processing unit that may be used to perform the operations of the HSI systems described herein, including real-time operations of an HSI system as part of an augmented reality system that provides real-time AR imaging in support of surgical intervention in some embodiments according to the invention.

With some implementations of the disclosed technology, the processor circuit may employ one or more processing units having more than one processor core. Accordingly, FIG. 10 illustrates an example of a multi-core processor circuit that may be employed with various embodiments of the disclosed technology. As seen in this figure, the processor circuit includes a plurality of processor cores. Each processor core includes a computing engine and a memory cache. As known to those of ordinary skill in the art, a computing engine contains logic devices for performing various computing functions, such as fetching software instructions and then performing the actions specified in the fetched instructions. These actions may include, for example, adding, subtracting, multiplying, and comparing numbers, performing logical operations such as AND, OR, NOR and XOR, and retrieving data. Each computing engine may then use its corresponding memory cache to quickly store and retrieve data and/or instructions for execution.

Each processor core is connected to an interconnect. The particular construction of the interconnect may vary depending upon the architecture of the processor circuit. With some processor cores, such as the Cell microprocessor created by Sony Corporation, Toshiba Corporation and IBM Corporation, the interconnect may be implemented as an interconnect bus. With other processor units, however, such as the Opteron™ and Athlon™ dual-core processors available from Advanced Micro Devices of Sunnyvale, Calif., the interconnect may be implemented as a system request interface device. In any case, the processor cores communicate through the interconnect with an input/output interface and a memory controller. The input/output interface provides a communication interface between the processor circuit and the bus. Similarly, the memory controller controls the exchange of information between the processor circuit and the system memory. With some implementations of the disclosed technology, the processor units may include additional components, such as a high-level cache memory accessible shared by the processor cores.

While FIG. 10 shows one illustration of a processor circuit hat may be employed by some embodiments of the disclosed technology, it should be appreciated that this illustration is representative only, and is not intended to be limiting. Also, with some implementations, a multi-core processor circuit can be used in lieu of multiple, separate processor units. For example, rather than employing six separate processor units, an alternate implementation of the disclosed technology may employ a single processor circuit having six cores, two multi-core processor circuits each having three cores, a multi-core processor circuit with four cores together with two separate single-core processor units, etc.

Returning now to FIG. 9, the interface device allows the processor circuit 103 to communicate with the co-processors through a communication interface. The communication interface may be any suitable type of interface including, for example, a conventional wired network connection or an optically transmissive wired network connection. The communication interface may also be a wireless connection, such as a wireless optical connection, a radio frequency connection, an infrared connection, or even an acoustic connection. The interface device translates data and control signals from the processor circuit and each of the co-processors into network messages according to one or more communication protocols, such as the transmission control protocol (TCP), the user datagram protocol (UDP), and the Internet protocol (IP). These and other conventional communication protocols are well known in the art, and thus will not be discussed here in more detail.

Each co-processor may include a memory, a processor circuit, an interface device, and, optionally, one more input/output devices connected together by a system bus. As with the processor circuit, the optional input/output devices for the servant computers may include any conventional input or output devices, such as keyboards, pointing devices, microphones, display monitors, speakers, and printers. Similarly, the processor circuits may be any type of conventional or custom-manufactured programmable processor device. For example, one or more of the processor circuits may be commercially generic programmable microprocessors, such as Intel™ Pentium® or Xeon™ microprocessors, Advanced Micro Devices Athlon™ microprocessors or Motorola 68K/Coldfire® microprocessors. Alternately, one or more of the processor circuits may be custom-manufactured processors, such as microprocessors designed to optimally perform specific types of mathematical operations. With some implementations of the disclosed technology, one or more of the processor circuits may be a Cell processor. The memory then may be implemented using any combination of the computer readable media discussed above. Like the interface device, the interface devices allow the co-processors to communicate with the processor circuit over the communication interface.

In the illustrated example, the processor circuit is a multi-processor circuit computer with multiple processor units, while each co-processor may have a single processor circuit. It should be noted, however, that alternate implementations of the disclosed technology may employ a processor circuit having single processor circuit. Further, one or more of the co-processors may have multiple processor circuits, depending upon their intended use, as previously discussed. Also, while only a single interface device is illustrated for both the processor circuit and the co-processors, it should be noted that, with alternate embodiments of the disclosed technology, either the processor circuit, one or more of the co-processors, or some combination of both may use two or more different interface devices or for communicating over multiple communication interfaces.

With various examples of the disclosed technology, the processor circuit may be connected to one or more external data storage devices. These external data storage devices may be implemented using any combination of computer readable media that can be accessed by the processor circuit 103. The computer readable media may include, for example, microcircuit memory devices such as read-write memory (RAM), read-only memory (ROM), electronically erasable and programmable read-only memory (EEPROM) or flash memory microcircuit devices, CD-ROM disks, digital video disks (DVD), or other optical storage devices. The computer readable media may also include magnetic cassettes, magnetic tapes, magnetic disks or other magnetic storage devices, punched media, holographic storage devices, or any other medium that can be used to store desired information. According to some implementations of the disclosed technology, one or more of the co-processors may alternately or additionally be connected to one or more external data storage devices. Typically, these external data storage devices will include data storage devices that also are connected to the processor circuit, but they also may be different from any data storage devices accessible by the processor circuit.

It also should be appreciated that the description of the computer network illustrated in FIG. 9 and FIG. 10 is provided as an example only, and it not intended to suggest any limitation as to the scope of use or functionality of alternate embodiments of the disclosed technology.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the various embodiments described herein. As used herein, the term "and/or" includes any and all combinations of one or more of the associated listed items.

The terminology used herein is for the purpose of describing particular embodiments only and is not intended to be limiting to other embodiments. As used herein, the singular forms "a", "an" and "the" are intended to include the plural forms as well, unless the context clearly indicates otherwise. It will be further understood that the terms "comprises," "comprising," "includes" and/or "including", "have" and/or "having" when used herein, specify the presence of stated features, integers, steps, operations, elements, and/or components, but do not preclude the presence or addition of one or more other features, integers, steps, operations, elements, components, and/or groups thereof. Elements described as being "to" perform functions, acts and/or operations may be configured to or other structured to do so.

Unless otherwise defined, all terms (including technical and scientific terms) used herein have the same meaning as commonly understood by one of ordinary skill in the art to which various embodiments described herein belong. It will be further understood that terms used herein should be interpreted as having a meaning that is consistent with their meaning in the context of this specification and the relevant art and will not be interpreted in an idealized or overly formal sense unless expressly so defined herein.

As will be appreciated by one of skill in the art, various embodiments described herein may be embodied as a method, data processing system, and/or computer program product. Furthermore, embodiments may take the form of a computer program product on a tangible computer readable storage medium having computer program code embodied in the medium that can be executed by a computer.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wired, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages, such as a programming language for a FPGA, Verilog, System Verilog, Hardware Description language (HDL), and VHDL. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

Some embodiments are described herein with reference to flowchart illustrations and/or block diagrams of methods, systems and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall support claims to any such combination or subcombination.

In the drawings, the shapes and dimensions of elements may be exaggerated for clarity, and the same reference numerals will be used throughout to designate the same or like elements. It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (i.e., "between" versus "directly between", "adjacent" versus "directly adjacent", etc.).

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated elements but do not preclude the presence or addition of one or more other elements.

While exemplary embodiments have been shown and described above, it will be apparent to those skilled in the art that modifications and variations could be made without departing from the spirit and scope of the present disclosure as defined by the appended claims.

What is claimed is:

1. A hyperspectral imaging system comprising:
   a first hyperspectral imaging camera configured to provide first hyperspectral image data of an object in a first field of view;
   a second hyperspectral imaging camera, separated from the first hyperspectral imaging camera, the second hyperspectral imaging camera configured to provide second hyperspectral image data of the object in a second field of view; and a processor circuit, operatively coupled to the first and second hyperspectral imaging cameras, the processor circuit configured to combine the first and second hyperspectral image data to generate a hypercube of data for the object comprising spectral data included in the first and second hyperspectral image data;

wherein the first hyperspectral image data includes a two dimensional array of spatial image data for the first field of view and first spectral data for each pixel in the two dimensional array of spatial image data for the first field of view;

wherein the second hyperspectral image data includes a two dimensional array of spatial image data for the second field of view and second spectral data for each pixel in the two dimensional array of spatial image data for the second field of view;

wherein the first spectral data includes first wavelength data over a first spectral range for each pixel in the two dimensional array of spatial image data in the first field of view;

wherein the second spectral data includes second wavelength data over a second spectral range for each pixel in the two dimensional array of spatial image data in the second field of view; and wherein the processor circuit is configured to combine the first and second wavelength data to provide the hypercube of data including a first spectral profile as a function of wavelength for each pixel in the two dimensional array of spatial image data for the first and second fields of view and configured to generate first and second derivatives of the first spectral profile of the wavelength for each pixel in the two dimensional array of spatial image data for the first and second fields of view to provide second and third spectral profiles, respectively.

2. The system of claim 1:
wherein the first hyperspectral image data comprises a first time sequence of first hyperspectral images including the first hyperspectral image data for each of the first hyperspectral images in the first time sequence; and
wherein the second hyperspectral image data comprises a second time sequence of second hyperspectral images including the second hyperspectral image data for each of the second hyperspectral images in the second time sequence.

3. The system of claim 2 wherein the first and second time sequences are generated by the processor circuit in real-time.

4. The system of claim 1 wherein the first and second spectral ranges are in a combined range of about 400 nm to about 2500 nm.

5. The system of claim 1 wherein the first and second spectral ranges are in a combined range of about 400 nm to about 1700nm.

6. The system of claim 1 wherein the first and second wavelength data is organized into a plurality of bins that are separated from one another by about 2 nm to about 10 nm.

7. The system of claim 1 wherein the first spectral profile represents reflected spectral flux for each for each pixel in the two dimensional array of spatial image data.

8. The system of claim 1 wherein the processor circuit is:
configured to provide the first, second, and third spectral profiles to a convolutional neural network trained to recognize indications of cancerous tissue within the object to generate indicia of at least a probability of cancerous tissue within the object; and
configured to map the indicia to a corresponding pixel in the two dimensional array of spatial image data to provide a diagnostic overlay.

9. The system of claim 8 further comprising:
an augmented reality (AR) head mounted system wirelesly operatively coupled to the processor circuit, wherein the processor circuit transmits the diagnostic overlay to the augmented reality head mounted system, wherein the AR head mounted system is configured to augment an image of the cancerous tissue, provided on a display of the AR head mounted system from a AR head mounted system camera, with the diagnostic overlay including the indicia of at least a probability of the cancerous tissue within the object.

10. The system of claim 9 further comprising:
a registration system coupled to the processor circuit, wherein the registration system is configured to provide a real-time position field of view of the AR head mounted system camera to the processor circuit, wherein the processor circuit is configured to provide updated diagnostic overlay to the AR head mounted system in response to changes in the real-time position field of view of the AR head mounted system.

11. A method of operating a hyperspectral imaging system, the method comprising:
receiving first hyperspectral image data of an object in a first field of view from a first hyperspectral imaging camera;
receiving second hyperspectral image data of the object in a second field of view from a second hyperspectral imaging camera that is separated from the first hyperspectral imaging camera; and
combining the first and second hyperspectral image data to generate a hypercube of data comprising reflected spectral flux data, wherein the first and second hyperspectral image data comprises respective first and second spectral profile $S_\lambda^{(0)}$ of spectral reflectance intensities of light reflected from an area of an object that corresponds to each pixel, and wherein each spectral reflectance intensity is measured in a discrete range of wavelengths, including visible, near-infrared and short-wave infrared wavelengths, the method further comprising:
(a) differentiating the spectral profile $S_\lambda^{(0)}$ to obtain a first derivative spectral profile $S_\lambda^{(1)}$ and a second derivative spectral profile $S_\lambda^{(2)}$;
(b) providing the spectral profile, the first derivative spectral profile and the second derivative spectral profile as inputs to a neural network configured to identify pixels associated with the spectral profile are cancerous;
repeating operations (a) and (b) to provide a 2D overlay image of the object; and
overlaying the 2D overlay image of the object onto an image of the object to provide a diagnostic image of the object indicating areas of cancerous tissue in the object to generate a diagnostic image.

12. The method of claim 11 wherein the first hyperspectral image data includes a two dimensional array of spatial image data for the first field of view and first spectral data for each pixel in the two dimensional array of spatial image data for the first field of view; and
wherein the second hyperspectral image data includes a two dimensional array of spatial image data for the second field of view and second spectral data for each pixel in the two dimensional array of spatial image data for the second field of view.

13. The method of Claim 11 wherein overlaying the 2D overlay image of the object onto the image of the object comprised:
providing the 2D overlay image of the object to an augmented reality (AR) head mounted system, wherein the AR head mounted system is configured to augment the image of the object from an AR head mounted system camera with the 2D overlay image of the object to provide the diagnostic image.

14. The method of claim 13 further comprising:
providing a real-time position field of view of the AR head mounted system camera;
providing updated 2D overlay image of the object to provide an updated diagnostic image diagnostic overlay to the AR head mounted system in response to changes in the real-time position field of view of the AR head mounted system.

15. A hyperspectral imaging system for detecting cancerous tissue areas in a tissue specimen comprising:
a translatable frame;
a first hyperspectral imaging camera, attached to the translatable frame, configured to focus on an area of interest of a tissue specimen and configured to generate a first hyperspectral image of the area of interest in a first spectral range;
a second hyperspectral imaging camera, attached to the translatable frame, configured to focus on the area of interest of the tissue specimen and configured to generate a second hyperspectral image of the area of interest in a second spectral range;
a processor circuit configured to control a position of the translatable frame to allow the first and second hyperspectral imaging cameras to scan a plurality of areas of the tissue specimen, including the area of interest and configured to combine the first and second hyperspectral images to provide a hypercube of data for the area of interest;
a first rotating frame coupling the translatable frame to the first hyperspectral imaging camera allowing the first hyperspectral imaging camera to rotate toward/away from the second hyperspectral imaging camera to change a first field of view of the tissue provided by the first hyperspectral imaging camera; and
a second rotating frame coupling the translatable frame to the second hyperspectral imaging camera allowing the second hyperspectral imaging camera to rotate toward/away from the first hyperspectral imaging camera to change a second field of view of the tissue provided by the second hyperspectral imaging camera, wherein the first and second rotating frames rotate independently of one another.

16. A method of operating a hyperspectral imaging system, the method comprising:
receiving first hyperspectral image data of an object in a first field of view from a first hyperspectral imaging camera, wherein the first hyperspectral image data includes a two dimensional array of spatial image data for the first field of view and first spectral data for each pixel in the two dimensional array of spatial image data for the first field of view and wherein the first spectral data includes first wavelength data over a first spectral range for each pixel in the two dimensional array of spatial image data in the first field of view;
receiving second hyperspectral image data of the object in a second field of view from a second hyperspectral imaging camera that is separated from the first hyperspectral imaging camera, wherein the second hyperspectral image data includes a two dimensional array of spatial image data for the second field of view and second spectral data for each pixel in the two dimensional array of spatial image data for the second field of view and wherein the second spectral data includes second wavelength data over a second spectral range for each pixel in the two dimensional array of spatial image data in the second field of view; and
combining the first and second hyperspectral image data to generate a hypercube of data comprising reflected spectral flux data that includes a first spectral profile as a function of wavelength for each pixel in the two dimensional array of spatial image data for the first and second fields of view and to generate first and second derivatives of the first spectral profile of the wavelength for each pixel in the two dimensional array of spatial image data for the first and second fields of view to provide second and third spectral profiles, respectively.

17. A hyperspectral imaging system for detecting cancerous tissue areas in a tissue specimen comprising:
a translatable frame;
a first hyperspectral imaging camera, attached to the translatable frame, configured to focus on a first field of view of an area of interest of a tissue specimen and configured to generate first hyperspectral image data of the area of interest in a first spectral range, wherein the first hyperspectral image data includes a two dimensional array of spatial image data for the first field of view and first spectral data for each pixel in the two dimensional array of spatial image data for the first field of view, wherein the first spectral data includes first wavelength data over the first spectral range for each pixel in the two dimensional array of spatial image data in the first field of view;
a second hyperspectral imaging camera, attached to the translatable frame, configured to focus on a second field of view of the area of interest of the tissue specimen and configured to generate second hyperspectral image data of the area of interest in a second spectral range, wherein the second hyperspectral image data includes a two dimensional array of spatial image data for the second field of view and second spectral data for each pixel in the two dimensional array of spatial image data for the second field of view, wherein the second spectral data includes second wavelength data over the second spectral range for each pixel in the two dimensional array of spatial image data in the second field of view;
a processor circuit configured to control a position of the translatable frame to allow the first and second hyperspectral imaging cameras to scan a plurality of areas of the tissue specimen, including the area of interest and configured to combine the first and second hyperspectral image data to provide a hypercube of data for the area of interest, wherein the processor circuit is configured to combine the first and second wavelength data to provide the hypercube of data including a first spectral profile as a function of wavelength for each pixel in the two dimensional array of spatial image data for the first and second fields of view and configured to generate first and second derivatives of the first spectral profile for each pixel in the two dimensional array of spatial image data for the first and second fields of view to provide second and third spectral profiles, respectively.

* * * * *